US005545275A

United States Patent [19]

Herrin et al.

[11] Patent Number: 5,545,275
[45] Date of Patent: Aug. 13, 1996

[54] METHOD FOR WELDING SEAMS IN DISPOSABLE GARMENTS

[76] Inventors: Robert M. Herrin, 5935 Groveline Dr., Orlando, Fla. 32810; John M. Tharpe, 2606 Northgate, Albany, Ga. 31707

[21] Appl. No.: 257,768

[22] Filed: Jun. 9, 1994

Related U.S. Application Data

[63] Continuation-in-part of Ser. No. 884,804, May 19, 1992, abandoned, which is a continuation-in-part of Ser. No. 442,215, Nov. 28, 1989, Pat. No. 5,308,345.

[51] Int. Cl.[6] .............................. A61F 13/15; B29C 65/08
[52] U.S. Cl. .................... 156/731; 2/400; 2/402; 156/308.4; 156/311; 156/580.1; 604/389
[58] Field of Search ................... 604/389; 2/400, 2/402; 156/73.1, 311, 580.1, 308.4, 308.2

[56] References Cited

U.S. PATENT DOCUMENTS

| | | | |
|---|---|---|---|
| 2,682,294 | 6/1954 | Langer | 156/311 X |
| 3,022,814 | 2/1962 | Bodine, Jr. | 156/73.1 |
| 3,505,136 | 4/1970 | Attwood | 156/73.1 |
| 3,756,878 | 9/1973 | Willot | 604/389 X |
| 3,765,973 | 10/1973 | Kramer | 156/73.1 |
| 3,816,211 | 6/1974 | Haigh | 156/311 X |
| 4,610,681 | 9/1986 | Strohbeen et al. | 604/396 |
| 4,646,362 | 3/1987 | Heran et al. | 2/400 |
| 4,862,673 | 9/1989 | Francioni | 156/515 X |
| 5,236,430 | 8/1993 | Bridges | 2/402 X |
| 5,246,433 | 9/1993 | Hasse et al. | 604/396 |
| 5,421,924 | 6/1995 | Ziegelhoffer et al. | 156/308.4 X |

FOREIGN PATENT DOCUMENTS

| | | |
|---|---|---|
| 0234658 | 9/1987 | European Pat. Off. . |
| 2235125 | 2/1991 | United Kingdom . |
| 2257652 | 1/1993 | United Kingdom . |

*Primary Examiner*—Jeff H. Aftergut

[57] ABSTRACT

Spaced seams in a disposable garment web containing a plastic component and moving rapidly along a direction of manufacture is formed by bringing an ultrasonic welder into pressurized contact with the machine web for a predetermined period of time, heating the web along the seam for a first segment of the predetermined period of time and then maintaining pressurization with the ultrasonic welder during a second segment of the predetermined time period without heat sufficient to permit the plastic material to resolidify.

6 Claims, 10 Drawing Sheets

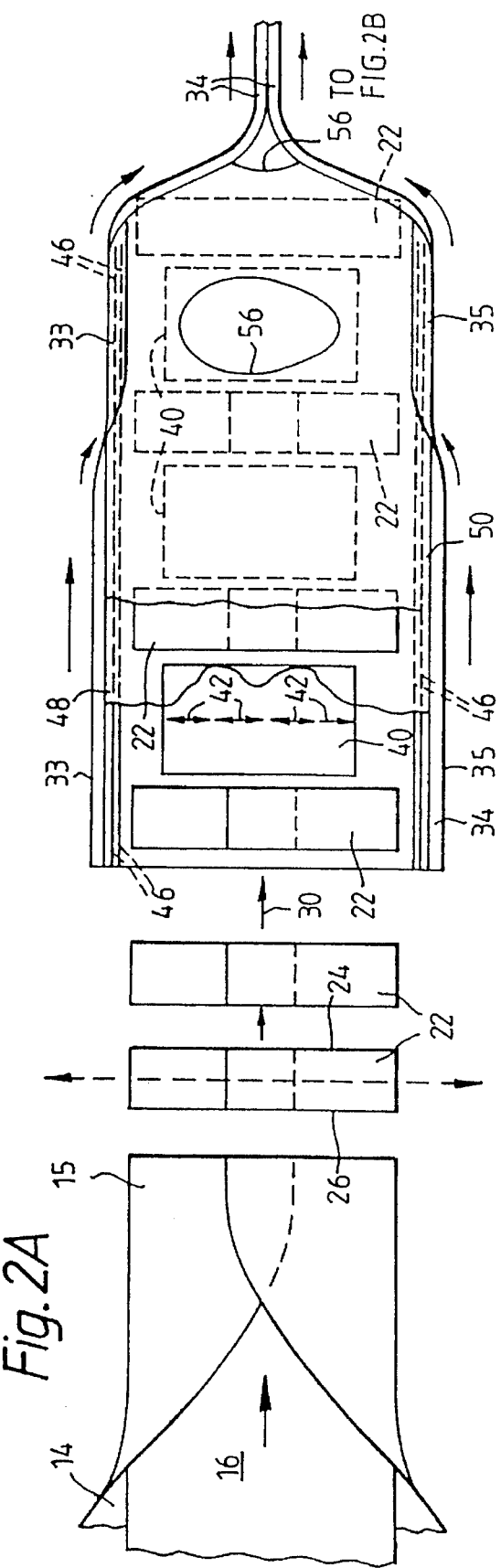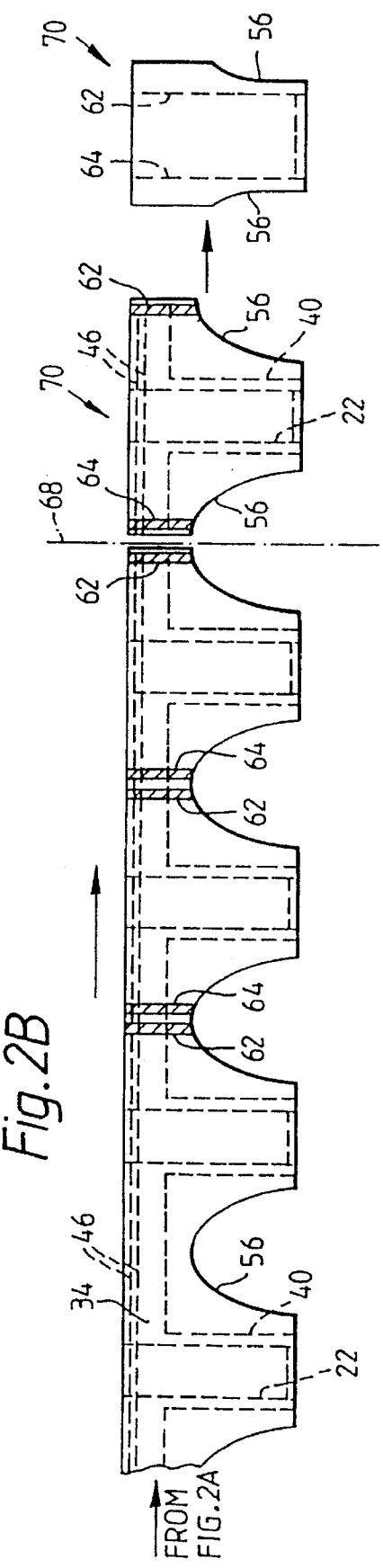
Fig. 2A
Fig. 2B

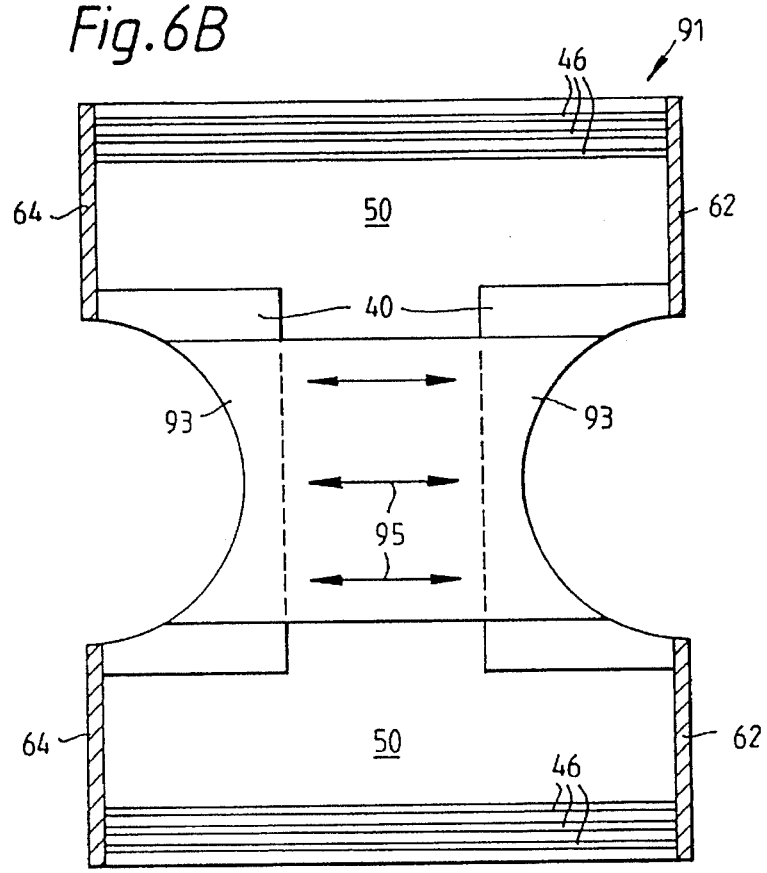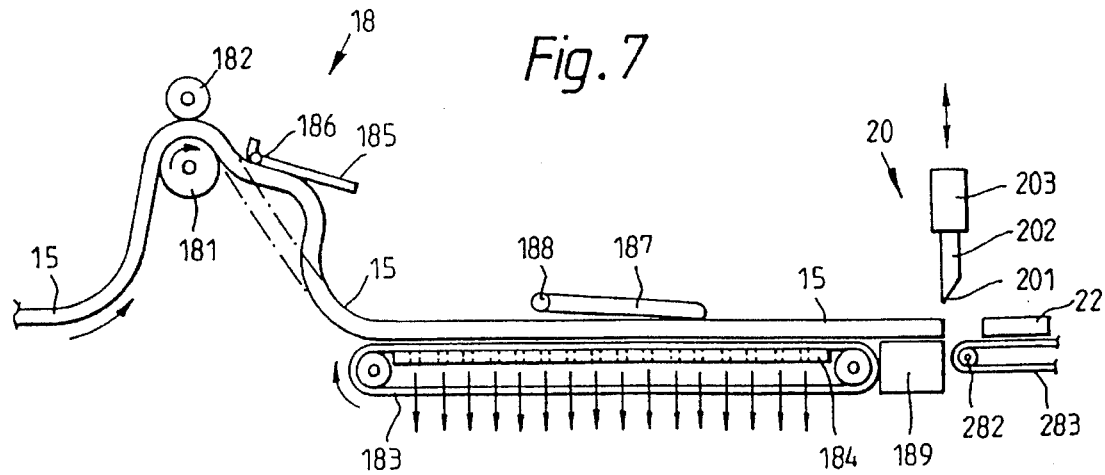

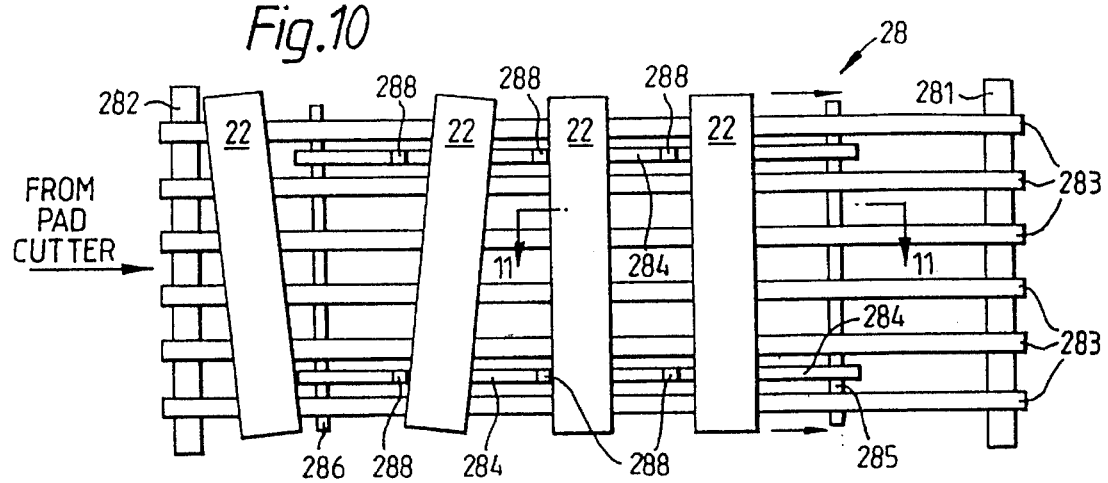
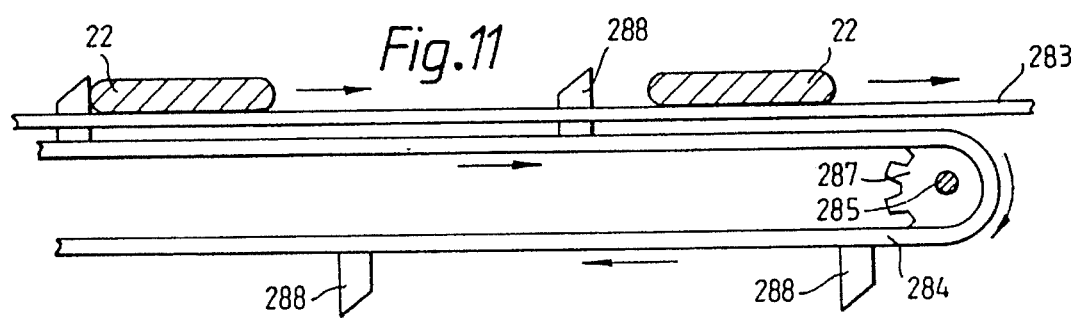
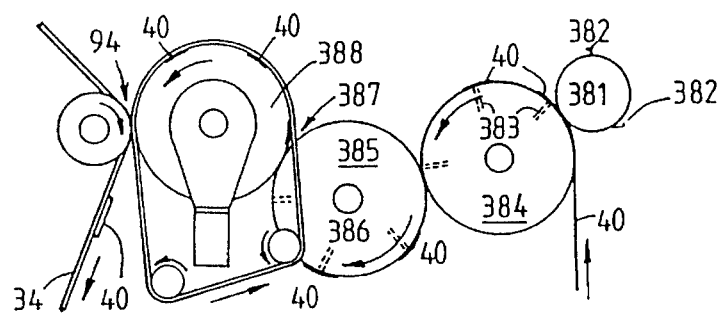

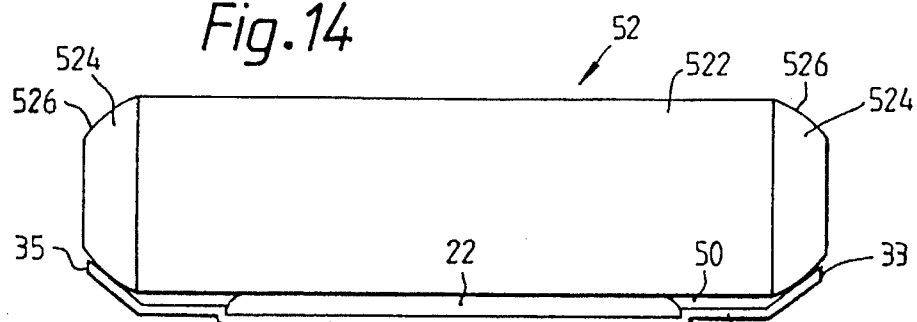
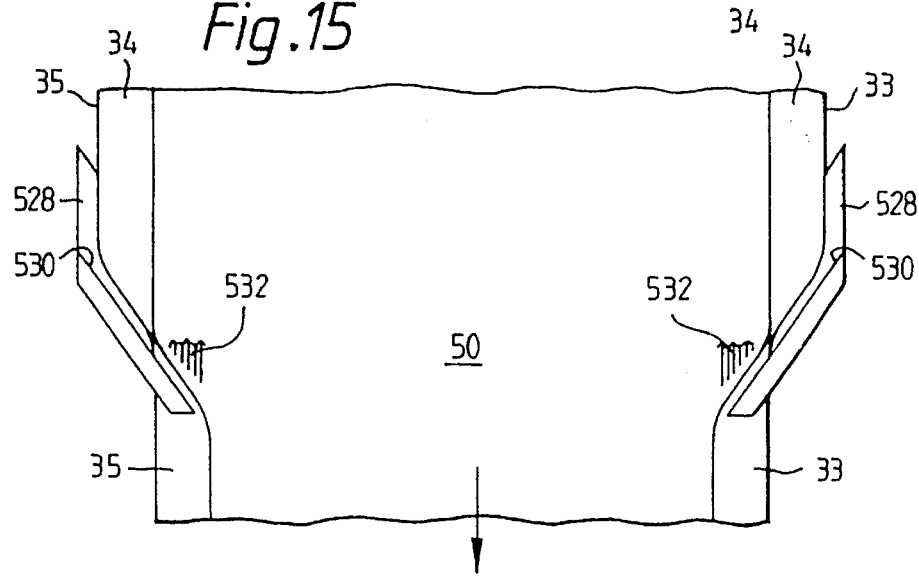
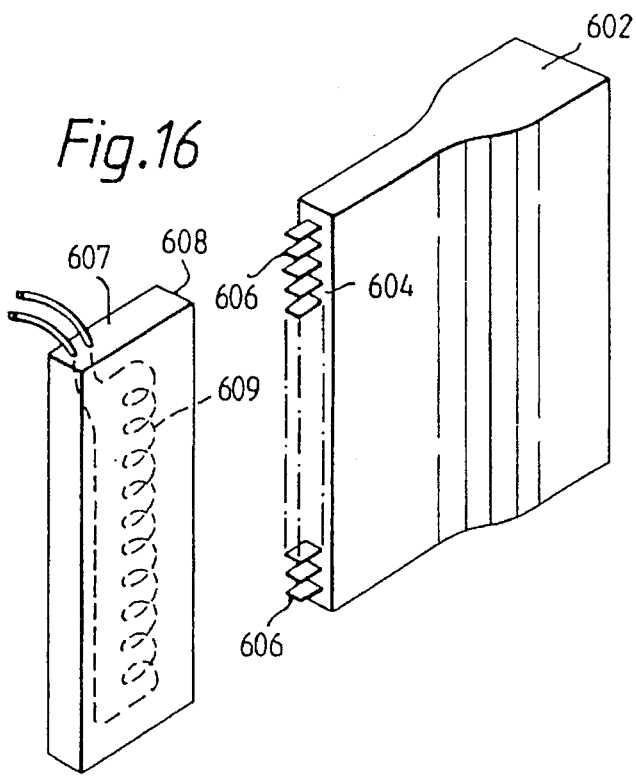

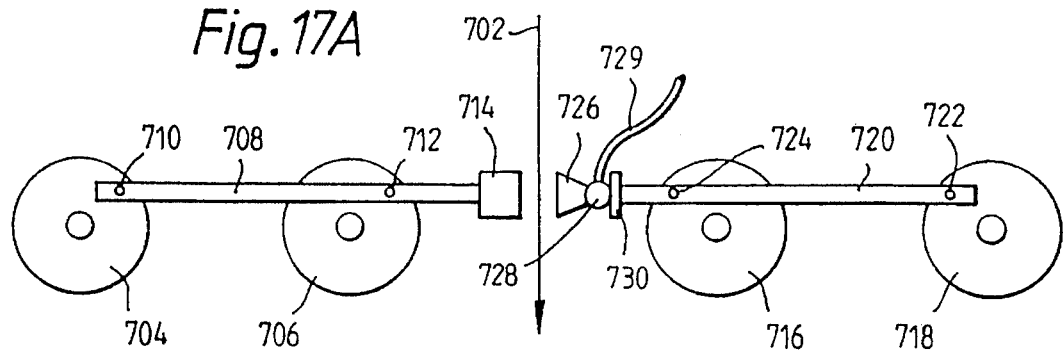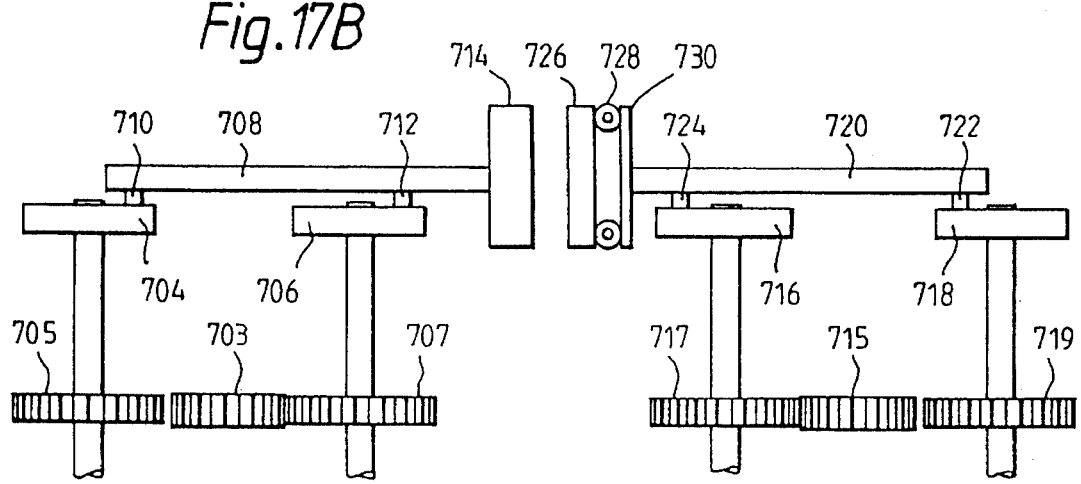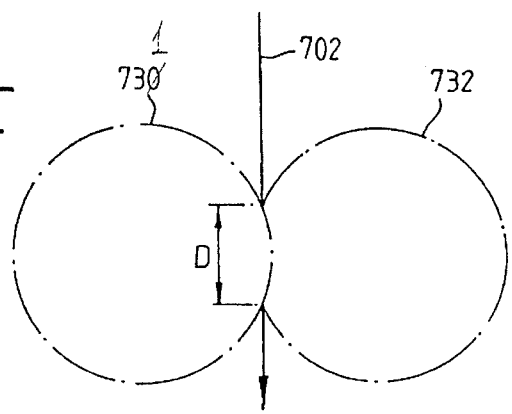

METHOD FOR WELDING SEAMS IN DISPOSABLE GARMENTS

This application is a continuation-in-part of application Ser. No. 07/884,804 filed on May 19, 1992, now abandoned, which application is a continuation-in-part of application Ser. No. 07/442,215 filed on Nov. 28, 1989, now U.S. Pat. No. 5,308,345.

BACKGROUND OF THE INVENTION

The present invention relates to disposable garments and methods and apparatus for making such garments.

The prior art teaches a wide variety of disposable diaper configurations, in which the finished diaper is a flat panel having adhesive tabs or the like, permitting the joinder of one end of the panel to the other, to fit the diaper panel from the infant's back, under the crotch and to the front of the waist. Examples of such arrangements are shown in the following U.S. Pat. Nos.: 3,081,772 to Brooks et al; 3,417,751 to Murdoch; 4,892,528 to Suzuki et al; and 5,064,489 to Ujimoto et al.

There have also been developed in the prior art a variation of finished disposable training pants for infants, in which the finished product has opposing side seams joining the front and back panels of the garment assembly. Examples of these arrangements are shown in the following U.S. Pat. Nos.: 4,743,239 to Cole; 4,743,241 to Igaue et al; 4,646,362 to Heran et al; 4,938,757 to Van Gompel et al; and 5,055,103 to Nomura et al; and 5,064,421 to Tracy.

The aforementioned U.S. Pat. No. 4,743,241 to Igaue et al discloses an elastic sheet adhered across the panel adjacent to the opposing leg openings, which serves as a liquid barrier for body fluids leaking from the center absorbent pad. A similar arrangement is disclosed in U.S. Pat. No. 3,417,751 to Murdoch.

A variety of techniques have been employed in the past in creating seams for disposable garments. For example, it is known to utilize an ultrasonic welder which comes into point contact with the machine web, in order to form such seams.

SUMMARY OF THE INVENTION

The present invention is directed to methods for welding together opposing panels of a disposable garment along spaced seams where at least one of the panels contains a plastic material capable of being rendered amorphous with heat. In accordance with the present invention, the method comprises the steps of bringing the two panels together under pressure during a predetermined period of time and heating the two panel portions during a first segment of the predetermined time period with sufficient heat and for a sufficient duration to render the plastic amorphous. The pressure is then maintained during a second segment of the predetermined of time without heat sufficient to permit the plastic material to resolidify and then the pressurization is withdrawn from the welded panels.

In accordance with the preferred form of the invention, the pressurization step during the predetermined period of time is carried out as the first and second panels are moving along a direction of manufacture; thus, the pressurization occurs over a defined dimension along that manufacturing path. Typically, one of the panels includes a non-plastic layer overlying the plastic material, with the preferred method further comprising the step of heating the plastic material through the non-plastic layer during at least the first segment of the predetermined period of time and while the first and second panels are moving along the direction of manufacture.

An ultrasonic welder which is mechanically disposed to move along the dimension generally parallel with the direction of manufacture with the disposable garment web is suitable for providing the required pressure during the predetermined period of time, and may be continuously recycled so as to engage the manufacturing web at downstream locations to create other seam welds. The desired heat is imparted to the plastic material by energizing the ultrasonic welder and permitting the transfer of ultrasonic energy to that material. It is also preferred that the ultrasonic welder is energized before engaging the web, prior to beginning the first time segment.

THE DRAWINGS

FIGS. 2A and 2B are top and front views, respectively, illustrating the component portions and manner of fabrication of disposable garments in accordance with the present invention and in which various locations along the direction of operation in FIGS. 2A and 2B generally correspond to the location of the various sections of the system illustrated in FIGS. 1A and 1B.

FIG. 6B is a top view of a third form of a disposable garment according to this invention.

FIG. 7 is a side elevation illustrating the accumulator section of the system shown in FIG. 1A.

FIG. 10 is a top plan view of the pad conveyor section of the system shown in FIG. 1A.

FIG. 11 is a cross section of a portion of the conveyor shown in FIG. 10, taken along the lines 11—11.

FIGS. 12 and 13 are top and side views, respectively, of the stretcher and applicator section of the system shown in FIG. 1A.

FIG. 14 is a front view of a portion of the edge-folding section in the system shown in FIG. 1A, and FIG. 15 is top view of that edge folding section.

FIG. 16 is a perspective view illustrating one form of the seam welding section of the system in FIG. 1B.

FIGS. 17A and B are top and side views illustrating construction details for a second form of the seam welding section.

FIG. 17C is a diagram illustrating the movement of the horn and anvil in the construction of FIGS. 17A and B.

Figure 18:
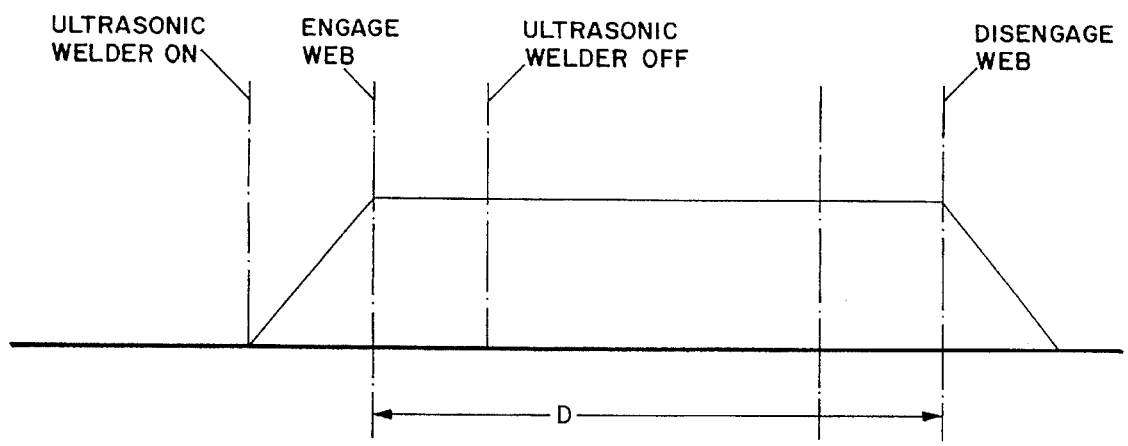

FIG. 18 is a timing diagram illustrating the preferred method in which the seam weld is formed utilizing an ultrasonic welder.

Figure 1A:
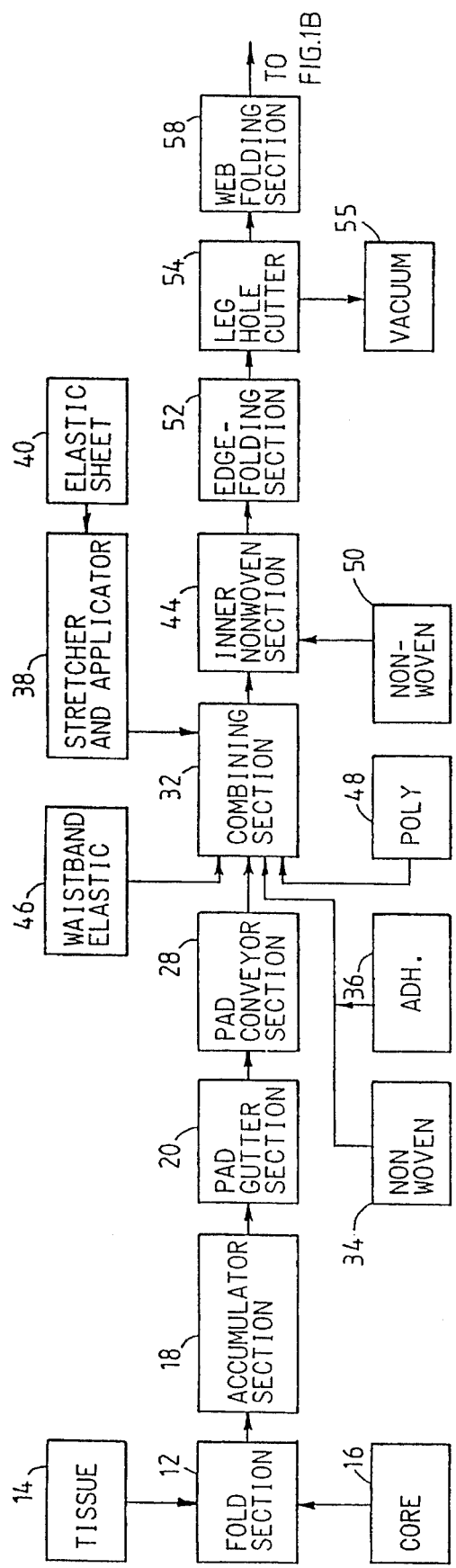
FIGS. 1A and 1B are flow charts illustrating the system, method and apparatus of the present invention, as used in the manufacture of disposal garments.
Figure 1B:
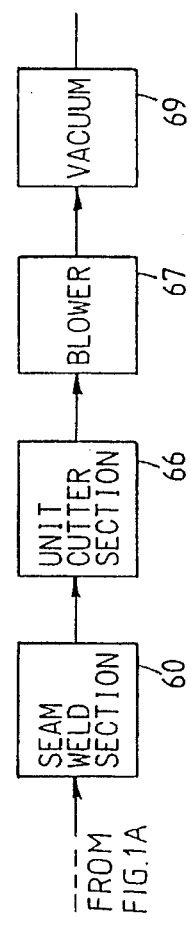

In FIGS. 7–16, three digit reference numerals are used to identify specific features of a corresponding portion of the system shown in FIGS. 1A and 1B, and in which the reference numeral for the section in FIGS. 1A and 1B has the same first two digit reference numeral (for example, in FIG. 7, three digit reference numerals 181, 182 and so forth refer to specific features of the accumulator section 18 in FIG. 1A).

DETAILED DESCRIPTION

The apparatus and method for making disposable garments will now be described with reference to FIGS. 1A and 1B, with concurrent reference to FIGS. 2A and 2B. Thereafter, three forms of disposable garments made according to the method and using the apparatus is described with reference to FIGS. 3–6A and B, followed by a description of specific features of the apparatus as shown in FIGS. 7–16, and an alternate seam weld construction in FIGS. 17A–C.

THE METHOD AND APPARATUS

Noting FIGS. 1A and 2A, the apparatus 10 includes a fold section 12 using conventional techniques to fold an absorbent core material 16 and an outer tissue 14, in order to form a web of absorbent pad material 15. The output of the fold section is passed into an accumulator section 18, which is shown schematically in FIG. 1A to be elevated with respect to the fold section 12, and the downstream pad cutter section 20. As illustrated in FIG. 2A, the absorbent pad web 15 is cut into individual pads 22, each having a forward edge 24 and a rear edge 26, by cutting along a direction lateral to the direction of manufacture, as illustrated by L-30. The individually cut pads 22 are passed into a pad conveyor section 28, and then to a combining section 32.

In the combining section 32, an outer non-woven layer 34 is extended along the direction of manufacture 30, and provided with an appropriate adhesive, generally over the entire exposed surface of the non-woven layer from 34. Waistband elastic strips 46 are extended along the adhesive-coated non-woven outer layer 34, again in the direction of manufacture 30, in order to provide a waistband elastic in a conventional manner. A liquid impervious liner 48 (for example, polyvinyl) is extended across the adhesive-coated non-woven layer 34, and then individual pads 22 are affixed to the exposed surface of the liner, using appropriate adhesives.

In accordance with the present invention, there is provided a source of elastic sheet material 40, for example polyurethane sheeting or polyethylene form, which is extended into a stretcher and applicator section 38, which is described in greater detail below with reference to FIGS. 12 and 13. As shown in FIG. 2A, the stretcher and applicator 38 cuts the elastic sheet into individual sheet segments 40, while simultaneously stretching each sheet segment 40 in a direction lateral to the direction of manufacture 30, as is depicted by arrows 42 in FIG. 2A, and generally under the stretch conditions discussed above; that it, a stretch on the order of five ounces per lineal inch for each inch of cross-width (i.e., twenty-five ounces for a five inch length of one inch wide elastic). The individual elastic sheets segments 40 may be affixed to either the liquid impervious liner 48, or to the outer non-woven layer 34, as shown in FIG. 2A. The polyvinyl liner 48 and the individual pads 22 are respectively affixed to the outer non-woven layer 34 and the liner 48 with a conventional adhesive 36.

The output of the combining section is fed into another section where an inner non-woven layer 50 is fixed to the assembly by an adhesive across the liner 48. As is shown in FIG. 2A, the inner non-woven layer 50 and the liner 48 have a lateral dimension somewhat less than the corresponding dimension of the outer non-woven layer 34, so that the outer non-woven layer has peripheral edges 33, 35 extending beyond the periphery of the other two layers. After deposition of the inner non-woven layer at section 44, the assembly is then fed into an edge folding section 52. As schematically depicted in FIG. 2A, the peripheral edges 33, 35 of the outer non-woven layer 34 are then folded across the periphery of the inner non-woven layer 50 and joined thereto with an adhesive, as described in greater detail below with reference to FIGS. 14 and 15.

The output from the edge folding section 52 is then fed into a leg hole cutting section 54, which is operated under a slight vacuum at 55, so as to remove the scrap without interfering with the manufacture of the assembly. Noting FIG. 2A, each leg hole 56 is cut centrally in the web defined by the layers 34, 48 and 50 between adjacent pads 22, and centrally within the peripheral boundary of a corresponding elastic sheet 40; preferably, the dimensions of the leg hole and the elastic sheet are selected so that a minimum of 0.5 inches of the elastic sheet, and suitably an even greater dimension, extend from the peripheral edge of the leg hole 56 to the boundary of the elastic sheet 40. It will of course be appreciated that the cutting of the leg hole 56 centrally in the elastic sheet 40 insures that the elastic sheet extends to the very edge of the leg hole. As will be discussed in greater detail below with reference to FIGS. 3–5, this particular feature enables the disposable garment to achieve a desirable inwardly rolled cuff which assists in defining a liquid barrier.

After passing out of the leg hole cutting section 54, the assembly is fed into a web folding section 58, where the entire web is folded upon itself, as depicted along the left hand side of FIG. 2B. The web is then fed into a seam welding section 60, where parallel seams are formed between the upper edge of the web and the upper extremity of each leg hole 56; preferably, this is achieved utilizing an ultrasonic welder and a rotating anvil which is heated to a temperature slightly below the melting point of the polyvinyl liner 48, and below the ignition temperature of the non-woven layers 34 and 50.

The output from the seam welding section is then passed into a unit cutter section 66, where the web is cut into individual garments 70. Each garment is then conveyed into a blower section 67, where air is blown into the individual garment, following which each individual garment is subjected to a vacuum at 69 to draw the intermediate seam welds inwardly to form a compact unit for packaging purposes.

A FIRST EMBODIMENT OF THE DISPOSABLE GARMENT (FIGS. 3–5)

Figure 3:
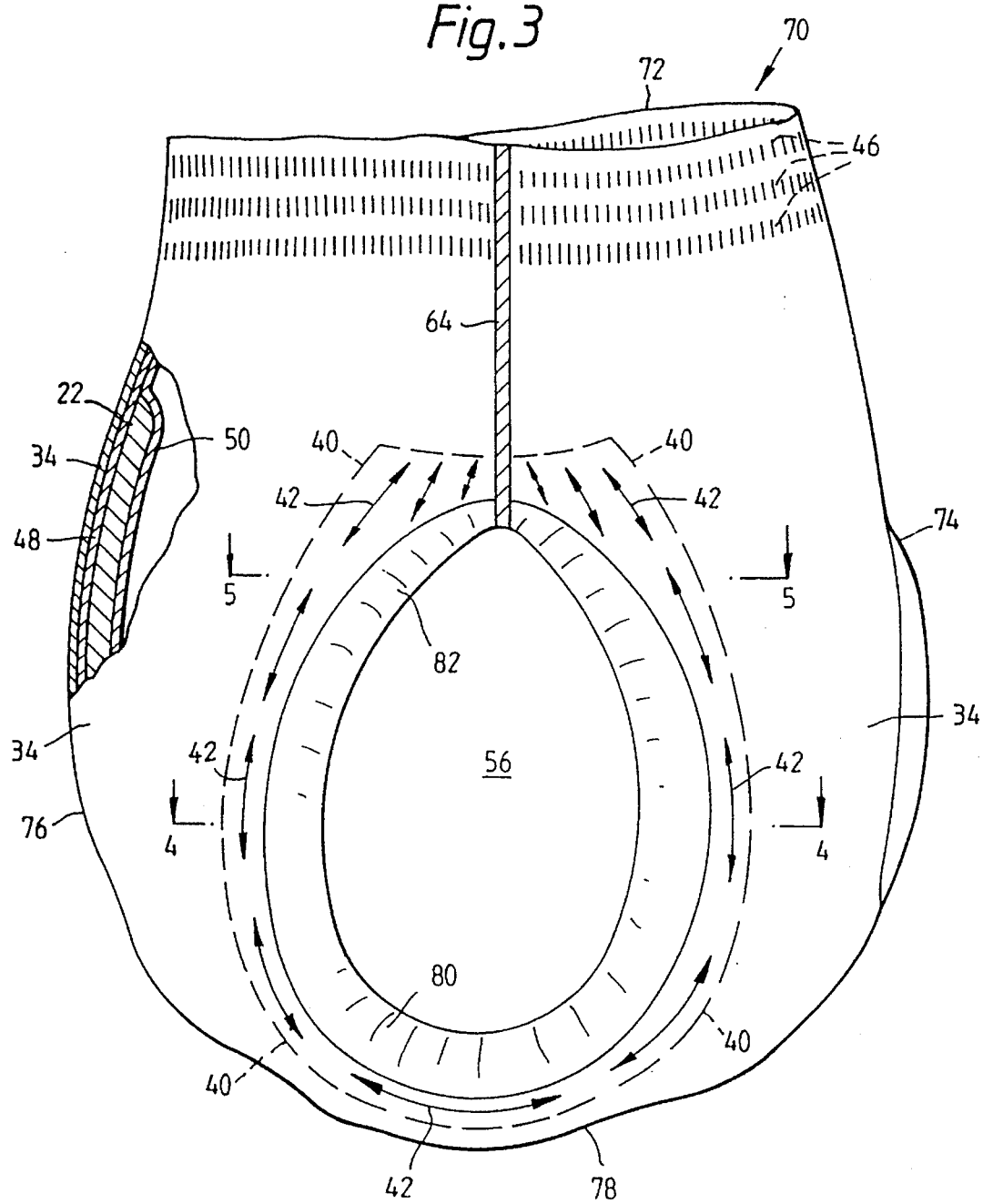
FIG. 3 is a side elevation, partially in cross section, of a disposable garment in accordance with the present invention.
Figure 4:
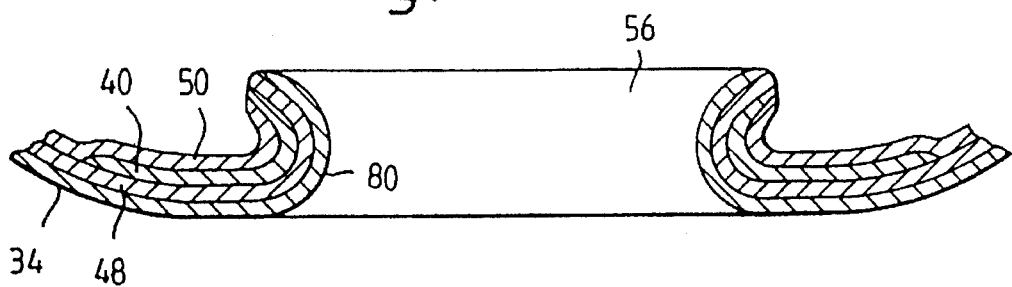
FIG. 4 is a cross section of a portion of the disposable garment shown in FIG. 3, taken along the line 4—4.
Figure 5:
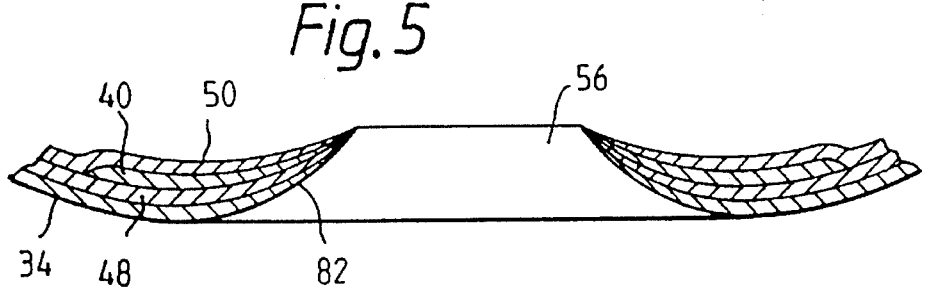
FIG. 5 is another cross section of a portion of the disposable garment shown in FIG. 3, taken along the line 5—5.

Construction details of a first form of the disposable garment 70 are depicted in FIGS. 3–5. As constructed, the garment 70 includes a waistband opening 72, a front panel 74, an opposing rear panel 76 and a crotch area 78; it will of course be understood that the front and back panels and the crotch area 74, 76 and 78 are formed from the assembly of materials in accordance with the method depicted in FIGS. 2A and 2B, and includes (as shown in the cut away portion in FIG. 3) the outer non-woven layer 34, the liner 48, absorbent pad 22 and inner non-woven layer 50, with the elastic waistbands 46 and seam 64.

The portion of the elastic sheet 40 remaining with the individual garment 70 after formation of the leg opening 56, folding of the web and welding of the seam 64 is depicted by a dotted line in FIG. 3. Arrows 42 also depict the direction of stretch of the elastic sheet 40. As discussed above, the cutting of the leg opening 56 through the field of the elastic sheet 40 to extend to the extreme periphery of the opening 56. This, together with the folding of the web to form the front and back panels 74, 76 relieves the stretching of the elastic sheet 40 along the periphery of the leg opening 56, and causes the elastic sheet along the periphery to roll into an inwardly-directed cuff along the periphery of the leg opening 56. However, because of the variance of the stretch represented by arrows 42 from the lower portion 80 of the leg opening 56 to the upper portion 82, the degree of roll of the cuff varies from the lower portion to the upper portion. This is shown by comparison of FIGS. 4 and 5, where the lower portion 80 of the rolled cuff is shown to be greater than the upper portion 82 of FIG. 5, this variance of the rolled cuff from the lower portion is desirable, since the upper portion does not require as great a roll in the cuff for purposes of providing a liquid barrier, and also provides greater comfort to the person wearing the garment 70.

OTHER FORMS OF THE DISPOSABLE GARMENT CONSTRUCTION (FIGS. 6A AND B)

Figure 6A:
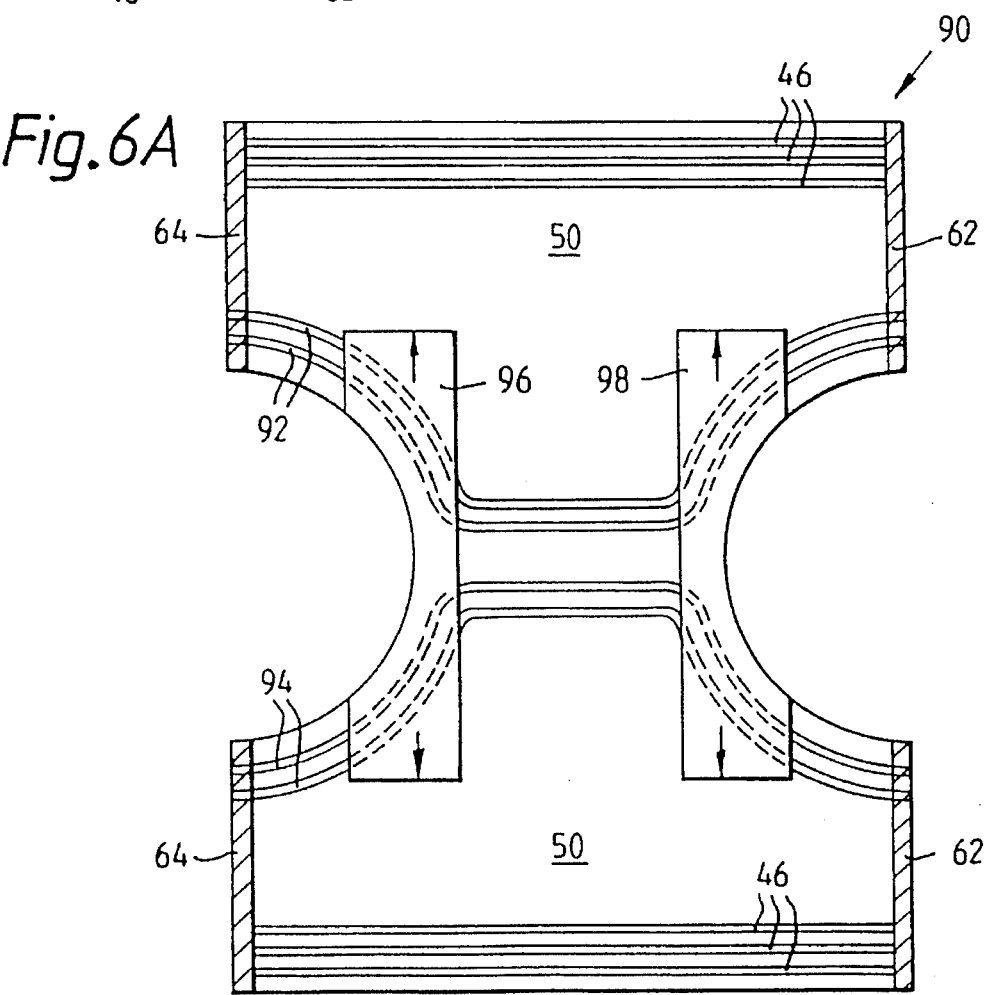
FIG. 6A is a top view of a second form of a disposable garment in accordance with the present invention.

A second alternate form of construction of the disposable garment in accordance with the present invention is shown in FIG. 6A and referred to generally by the reference numeral 90.

Disposable garment 90 includes various features of the garment 70 shown in FIGS. 3–5, which are referred to by the same reference numerals, including waistband elastic 46, seams 62, 64, inner non-woven layer 50, pad 22 and leg openings 56. The construction of disposable garment 90 from the construction of garment 70 in FIG. 3 through the use of elastic bands 92 and 94 which extend continuously around the periphery of opposite sides of each leg opening and across a portion of the same area covered by elastic sheets 96, 98 and also across the crotch area of the garment 90 to the opposite leg opening 56. Further, the elastic sheets 96, 98 may be drawn back slightly from the respective seams 64, 62 so as to extend essentially about the peripheral edge of the lower portion of the leg opening 56 after being folded.

A third form of construction of a disposable garment in accordance with the present invention is shown in FIG. 6B and referred to there by the reference numeral 91.

The disposable garment 91 also includes the various features of the garments 70 and 90 shown in FIGS. 3–5 and 6A, to the extent that those various features are referred to by the same reference numerals. Additionally, the garment 91 includes a second layer of elastic sheeting extending between the leg openings, and longitudinally stretched in the direction of the arrows 95 in FIG. 6B. The stretched elastic layer 93 avoids the necessity for providing the elastic bands 92 and 94 of FIG. 6A, while at the same time providing a uniform gathering of material in the crotch area of the garment 91.

THE ACCUMULATOR SECTION (FIG. 7)

Details of the accumulator section 18 of FIG. 1A are shown in FIG. 7.

As shown on the left hand side of FIG. 7, the absorbent pad web 15 is extended across elevated rollers 181, 182 which operate continuously to receive the feed of the web 15. The rollers 181, 182 then feed the web 15 downwardly across an indexing conveyor 183, which preferably consists of a wire mesh extending across a fixed vacuum plate 184 having holes therein permitting a vacuum to be drawn, as shown by arrows. The accumulator section 18 further includes a control plate 185 pivoted at 186, and extending across the web 15 somewhat below the continuous feed rollers 181, 182. Similarly, there is a pressure rod 187 pivoted at 188 extending across the absorbent pad web 15 and over the indexing conveyor 183.

In operation, the absorbent pad web 15 is drawn into fixed engagement with the mesh surface of the indexing conveyor 183 via the vacuum plate 184. The indexing conveyor 183 is operated on a "stop-start" or intermittent basis, as required by the operation of the reciprocating cutting blade 20 described below in greater detail with reference to FIGS. 8 and 9, but the details of which are also depicted in FIG. 7. Thus, the rollers 181 and 182 are continuously feeding the web 15 onto a conveyor which only operates on an intermittent basis; therefore, the web 15 is subjected to a buckling, as shown below the control plate 185. The degree of buckle is controlled by the plate 185, to insure that the direction of the web continues along the surface of the intermittent indexing conveyor 183. The pressure rod 187 also insures that any buckling does not extend beyond the central area of the indexing conveyor 183.

As shown on the right hand side of FIG. 7, the indexing conveyor 183 forces the absorbent pad web 15 across a fixed mandrel 189 in the throat of the cutting section 20, described next.

THE PAD CUTTING SECTION (FIGS. 8 AND 9)

As discussed briefly above, the pad cutting section 20 utilizes a reciprocating "guillotine"-type of cutter, which achieves certain benefits with respect to the formation of the cut edge in the absorbent pads 22.

Figure 8:
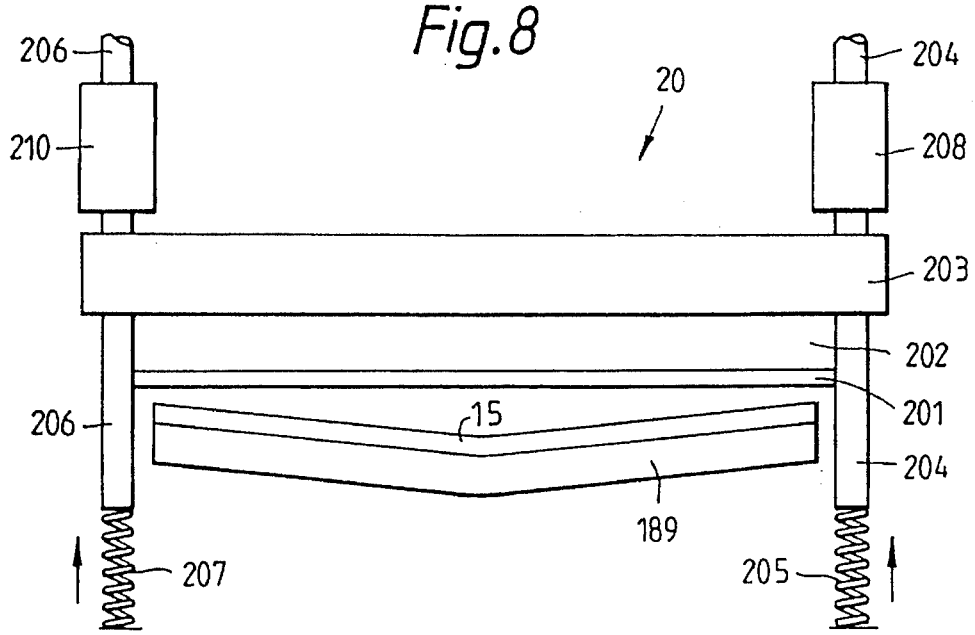
FIG. 8 is front elevation and FIG. 9 is a side elevation, both illustrating the features of the reciprocal knife cutting section of the system of FIG. 1A.

Referring to FIG. 8, the cutting section 20 includes a blade 202 terminating in a cutting edge 201, and carried by a cross plate 203 extending across the machine direction. The plate 203 is carried by reciprocating rods 204, 206 which are supported by springs 205, 207 for biasing in an upward direction. The reciprocating rods 204, 206 are supported by respective bearing blocks 208, 210. As shown in the front view of FIG. 8, the mandrel 189 has a V-configuration, such that the absorbent pad web 15 is sheared downwardly from each side to the central portion of the mandrel.

Figure 9:
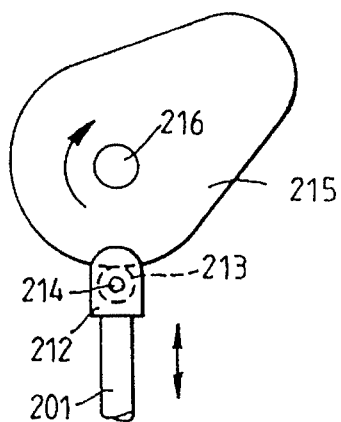

Noting FIG. 9, the reciprocating motion of the rods 204, 206 is controlled by an eccentric 215 rotating about a shaft 216, and engaging a rotating element 213 mounted on a pivot axis 214 and which is supported by a yoke 212 at the upper extremity of each rod 204, 206. The use of an eccentric cam surface to control the operation of the cutting blade 201, together with the shape of the cutting throat defined by mandrel 189 insures a smooth, even and sharp cut through the absorbent pad web 15, to define individual pads 22.

PAD CONVEYOR SECTION (FIGS. 10 AND 11)

Details of the pad conveyor section 28 of FIG. 1A are shown in FIGS. 10 and 11. The pad conveyor includes a pair of rotating shafts 281, 282 which extend laterally across the direction of manufacture, and support plural vinyl conveyor straps 283 along the manufacturing direction. As is depicted in FIG. 7, the conveyor webs 283 are extended into close proximity to the throat of the pad cutter 20.

A pair of chain drives 284 are supported parallel to and underneath the webbing 283, each chain drive 284 spaced between two of the webbing strips. The chain drives are supported by shaft 285 and an eccentric drive 287 (FIG. 11). Plural straightening dogs 288 are dimensioned vertically to extend upwardly from the respective chain drives 284 and above the level of the webbing strips 283. As is depicted in FIG. 10, the eccentric drive 287 imparts a "slow-fast-slow" pace to the movement of the straightening dogs, in order that the dogs may first extend upwardly between adjacent strips 283, then be speeded up to engage the backside of a corresponding pad 22 to straighten the position of any misaligned pad across the lateral direction, and then slow down and back away from the back edge of the corresponding pad, before rotating underneath the chain drive as shown in FIG. 11. Of course, the pad 22 is then discharged from the pad conveyor 28 on the right hand side of FIG. 10, and progresses to the combining section 32 (FIG. 1A).

STRETCHER AND APPLICATOR SECTION (FIGS. 12 AND 13)

As shown in FIG. 13, a web of the elastic sheet 40 (i.e., urethane foam or polyethylene) is passed into a knife roller 381 having knife blades 382, at which point the web of elastic sheet is cut into individual sheet segments 40. The knife roller 381 cuts the elastic sheet lengths 40, and vacuum chucks 383 on anvil 384 carries the elastic sheet lengths 40 to a transfer roller 385.

Figure 12:
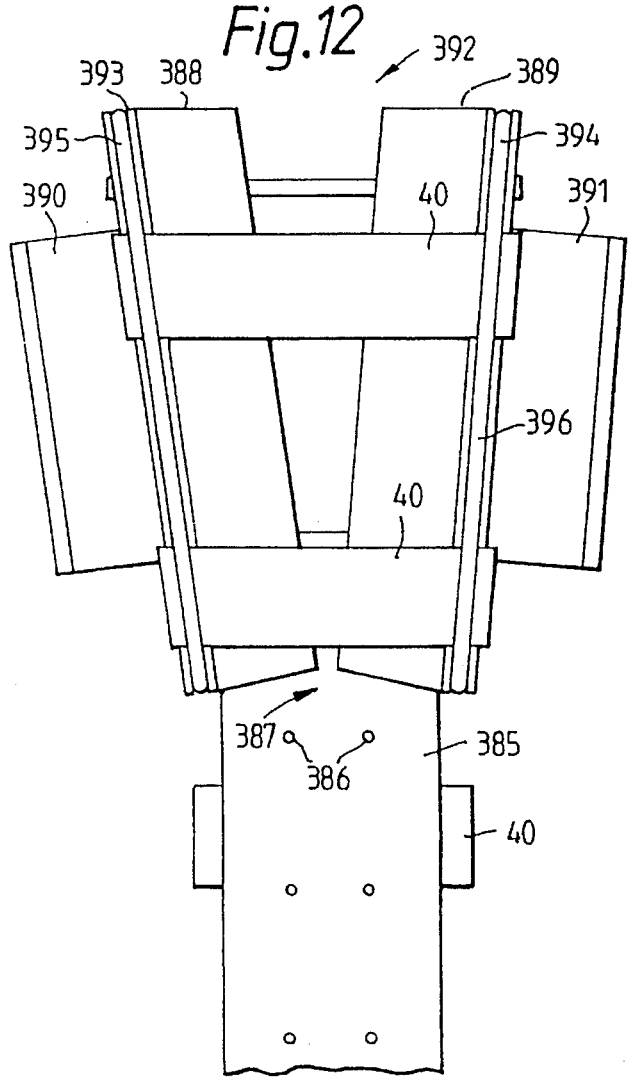

Noting both FIGS. 12 and 13, at an appropriate transfer point, the individual elastic sheets 40 are received along the surface of the transfer roller 385 which also includes vacuum chicks 386. The vacuum chucks 386 hold the individual elastic lengths 40 across the transfer surface of the transfer roller 385, until such time as the individual sheets 40 are fed into an entry point 387 of stretching rollers 388, 389. As is particularly shown in FIG. 12, the crosswise dimension of the transfer surface of the transfer roller 385 is substantially less than the lengthwise dimension of each elastic sheet 40, and is approximately equal to or less than the inner spacing between the stretching rollers 388, 389 at the entry point 387.

The stretching rollers 388,389 are mounted on respective hubs 390, 391, each of which may be individually adjusted at an outwardly skewed angle from the entry point 387 to an exit point 392. Each rotating stretching roller 388, 389 also includes a corresponding peripheral groove 393, 394 across which passes a corresponding smooth surface gripping belt 395, 396, each of which is dimensioned to fit within the corresponding peripheral groove 393, 394. As each gripping belt 395, 396 approaches the periphery of the corresponding roller 388, 389 at the entry point 387, an adjacent one of the elastic sheets 40 are picked up at the transfer point by the gripping belts and pinched into the corresponding groove 393, 394. As the skewed rollers 388, 389 are rotated, the gripping belts hold the sheets in place, and the skewed angle effectuates the desired degree of stretching. Thereafter, as is shown in FIG. 13, the individual sheets 40 are discharges at area 392 onto the web of the outer non-woven layer 34.

EDGE FOLDING SECTION (FIGS. 14 and 15)

The edge folding section 52 includes a pressure roller 522, under which the combined web assembly including the outer non-woven layer 34, liner (not depicted in FIG. 14), absorbent pad 22 and inner non-woven layer 50 are all passed. As is illustrated in FIG. 14, the pressure roller 522 includes inwardly tapered, low friction surfaces which are dimensioned to engage only the extended edge portions 33, 35 of the outer non-woven layer 34. Because the tension of the web is relieved by the taper 526 on the in caps 524, the edge portions 33, 35 are lifted upwardly. Thereafter, the web is passed across edge folders 528, each of which includes a tapered fold surface 530 for receiving the elevated edge portions 33, 35. A glue joint 532 is then directed across the outer edge of the inner non-woven layer 50, for receiving the folded edges 33, 35 of the outer non-woven layer 34.

SEAM WELD SECTION (FIGS. 16) AND 17A–C

As discussed above, the seam weld section 60 (FIG. 1B) utilizes an ultrasonic welder including weld head 602 having a face 604 with protruding weld pins 606. In accordance with the present invention, the pins 606 are sharpened to a sufficient degree to insure penetration through the entire web assembly, including the outer non-woven layer 34, elastic sheet 40, liner 48 and inner non-woven layer 50. Further in accordance with the present invention, the ultrasonic welder is operated in conjunction with a rotating anvil 607 having an anvil face 608 which is heated by an internal heating coil 609 to a temperature which is slightly below the melting temperature of the polyvinyl liner 48, and of course below the ignition temperature of the inner and outer non-woven layers 34, 50. It has been found that this particular arrangement shown in FIG. 16 provides desirable seam welds in a facile manner.

A second form of the seam welding section is depicted in FIGS. 17A–C. In this arrangement, the seam welding section includes opposing pairs of rotating drive wheels 704, 706 and 716, 718. Each pair of drive wheels is pivotally connected respectively at 710, 712 and 722,724 to a corresponding drive rod 708, 720. (As shown in FIG. 17B, each of the drive wheels is in turn rotated by a corresponding shaft and gear arrangement, including corresponding gears 795, 707 and 717, 719, with each the drive gear being driven by a respective pinion 703, 715).

A conventional ultrasonic horn 714 is mounted on the forward extremity of the drive rod 708, and a conventional ultrasonic anvil 726 is mounted at the extremity of the second drive rod 720. In accordance with the present invention, the anvil is coupled to a back plate 730 via an air bladder 728 which is capable of being alternately inflated and deflated from an air supply 729. This construction permits the anvil 726 to be inflated outwardly toward the horn 714, and also imparts a significant degree of "give" to the anvil 726 via the air bladder 728.

In operation, rotation of each pair of drive wheels 704, 706 and 716, 718 results in the reciprocal movement of the corresponding drive rod 708, 720 toward the machine web, represented by arrow 702 in FIGS. 17A and 17C. It will of course be appreciated by those skilled in the ultrasonic welding art that without the presence of the compressible bladder 728, there is only one tangential point where the ultrasonic horn 714 and the anvil 726 may come in contact with each other, in order to avoid any damage to either part. However, with the provision of the inflatable bladder 728, the anvil 726 is imparted with a significant degree of "give" or compressibility, thereby permitting the horn 714 and the anvil 726 to be in contact with each other for a much greater period of time during movement of the web (represented by arrow 702) along the direction of travel. This results in a much better forming of weld seams like seam 62 and 64 in FIG. 2B. This greater dimension of contact is represented by dimension D in FIG. 17C.

As is illustrated by the timing diagram of FIG. 18, it is preferred that the heating of the plastic material by the ultrasonic horn 714 and anvil 726 (FIG. 16) take place only for a first segment of the predetermined period of time during which the ultrasonic welder is engaged with the web along the dimension D. To achieve this, the ultrasonic welder is first turned on prior to the time that the horn 714 and anvil 726 engage the machine web, and is maintained on for a brief segment during movement along dimension D, after which the welder is turned off. As required, the welder and/or the web may also be cooled with air nozzles (not shown) or the heat may simply be permitted to dissipate into the ambient. During the remainder of the engagement of the welder with the machine web during the second time segment, it will of course be understood that pressure between the horn 714 and anvil 726 is maintained. It will also be understood that while the web is heated, the polyvinyl liner 48 is rendered amorphous, but resolidifies during the period in which the ultrasonic welder maintains pressurization against the machine web after the heat is turned off. At the end of the dimension D, the ultrasonic welder then disengages the web and is recycled to form another downstream seam. By way of example only, typical time periods for performing a seam weld at a nominal web speed of 100 garments per minute, are as follows: the predetermined time period is on the order of 150 milliseconds; the first time segment is about 30–50 milliseconds; and the second time segment is about 100–120 milliseconds. Typically, the dimension D is on the order of 3.5 inches, and the welder is turned at least about 50 milliseconds prior to engaging the web. As the web speed is changed, these time periods vary. As the web speeds are increased, it has been found that increased pressurization of the bladder 728 insures proper weld formation.

SUMMARY

There has been disclosed above a system and method for manufacturing disposable garments, the system including various apparatus features. Further, the disposable garments 70 and 90 of FIGS. 3–6 provide a cuff which extends inwardly from the plane of the leg hole, to provide a liquid barrier at least in the region of the lower portion of the leg opening. This is achieved utilizing an elastic sheet which may be stretched to a sufficient degree to insure achieving the desired rolled cuff feature, and in a manner which lends itself to high speed, low cost manufacturing techniques.

This concludes the description of the preferred embodiments. A reading by those skilled in the art will bring to mind various changes without departing from the spirit and scope of the invention. It is intended, however, that the invention only be limited by the following appended claims.

What is claimed is:

1. A method for welding together with a movable ultrasonic welder opposing moving panels which are to be joined together to form a disposable garment in a direction of manufacture, at least one of which panels contains a plastic material capable of being rendered amorphous with heat, the welding method comprising the steps of:

providing an ultrasonic welder movable along a portion of the direction of manufacture;

bringing the two panels together and pressurizing at least a portion of each panel into contact with the other panel using the ultrasonic welder during a predetermined period of time;

carrying out the pressurizing step during the predetermined period of time while the panels and the ultrasonic welder are moving continuously together along the direction of manufacture;

heating the two panel portions using the moving ultrasonic welder to heat the plastic material with ultrasonic energy during a first segment of the predetermined period of time with sufficient heat and for a sufficient duration to render the plastic amorphous;

maintaining pressurization using the ultrasonic welder while the ultrasonic welder continues to move together with the panels during a second segment of the predetermined period of time without heat sufficient to permit the plastic material to solidify; then withdrawing the pressurization of the ultrasonic welder from the welded panels; and wherein the second segment of the predetermined period of time is substantially greater than the first segment.

2. The method recited in claim 1 wherein each panel includes a non-plastic layer overlying the plastic material, and further comprising the step of heating the plastic material through the non-plastic layer and during at least the first segment of the predetermined period of time while the first and second panels are moving continuously along the direction of manufacture.

3. The method recited in claim 1 wherein the heating step comprises the step of energizing the ultrasonic welder and then contacting the panels with the ultrasonic welder.

4. The method recited in claim 1 wherein the pressurizing step further comprises the step of reciprocally moving components of the ultrasonic welder into and out of contact along a dimension while the panels are moving along the direction of manufacture.

5. The method recited in claim 4 further comprising the step of controlling the temperature of a component of the ultrasonic welder.

6. The method recited in claim 1 wherein the second segment of the predetermined period of time is on the order of at least about twice the first segment.

\* \* \* \* \*